(12) United States Patent
Maingault et al.

(10) Patent No.: US 7,923,596 B2
(45) Date of Patent: Apr. 12, 2011

(54) METHOD AND SYSTEM FOR PRODUCING DRESSING PRODUCTS OF POLYMER FIBRES USEFUL FOR COVERING MOIST WOUNDS

(75) Inventors: Philippe Maingault, Doue la Fontaine (FR); Christophe Pecoult, Boege (FR)

(73) Assignee: Les Laboratoiress Brothier, Nanterre (FR)

( * ) Notice: Subject to any disclaimer, the term of this patent is extended or adjusted under 35 U.S.C. 154(b) by 44 days.

(21) Appl. No.: 12/072,117

(22) Filed: Feb. 21, 2008

(65) Prior Publication Data

US 2008/0287853 A1 Nov. 20, 2008

Related U.S. Application Data

(62) Division of application No. 11/004,632, filed on Dec. 2, 2004, now abandoned.

(30) Foreign Application Priority Data

Dec. 2, 2003 (FR) ...................................... 03 14145

(51) Int. Cl.
*A61F 13/00* (2006.01)

(52) U.S. Cl. .............................. 602/41; 602/48; 602/900

(58) Field of Classification Search ................... 602/48, 602/900; 264/181, 164
See application file for complete search history.

(56) References Cited

U.S. PATENT DOCUMENTS

| | | | | |
|---|---|---|---|---|
| 1,732,592 A | * | 10/1929 | Cannon ............................. | 57/12 |
| 3,707,838 A | * | 1/1973 | Dorschner et al. ................... | 57/2 |
| 5,976,439 A | * | 11/1999 | Mahoney et al. ............. | 264/181 |

* cited by examiner

*Primary Examiner* — Kim M Lewis
(74) *Attorney, Agent, or Firm* — Novak Druce + Quigg; Gregory A. Nelson; Michael P. Byrne

(57) ABSTRACT

A method and system for producing an improved dressing product, useful for covering/protecting a moist wound is disclosed. The dressing product comprising fibers of a spinnable polymer forming a twisted ribbon. By virtue of this twisting, the fibers, in particular at the periphery of the ribbon, are connected to one another so as to afford better mechanical cohesion and a smoother outer appearance, without affecting the action of absorption, dilation and gel formation for extracting the biological fluid, nor the action of retention of proteins and other cellular and bacterial waste matter which would impede the phenomenon of cicatrization. The ribbon twisting equipment comprises a conical bowl (1) for driving fibers in rotation with a twisting die (3) in its narrowed downstream part (2), and a gear mechanism (4) for driving in rotation.

6 Claims, 2 Drawing Sheets

METHOD AND SYSTEM FOR PRODUCING DRESSING PRODUCTS OF POLYMER FIBRES USEFUL FOR COVERING MOIST WOUNDS

CROSS-REFERENCE TO RELATED APPLICATIONS

This application is a divisional of U.S. patent application Ser. No. 11/004,632 filed Dec. 2, 2004 now abandoned, which is incorporated herein by reference. U.S. patent application Ser. No. 11/004,632 takes priority from French Application No. 0314145 filed on Dec. 2, 2003.

BACKGROUND OF THE INVENTION

1. Field of the Invention

The present invention generally relates to dressing products such as a bandage or other sterile covering that is put on a wound to protect it from infection or further damage. More particularly, the present invention concerns a dressing product composed of fibres of a spinnable polymer, and a method and system for producing the dressing product, useful for covering haemostatic as well as exudative wounds.

2. Description of the Related Art

Dressing products, in the form of a ribbon or wick, are often used for moist wounds that produce exudates, for example, bedsores, post-operative wounds, and deep wounds such as cavities. Dressing products can also be used in intranasal surgery, in the upper airways of the nasal fossae, or for stopping nose bleeds with short wicks, which is also called tampons.

In making most prior art dressing products, consideration is often given to an alginate of a metal chosen from the family of polyvalent metals, except for magnesium, and, more particularly, a calcium alginate.

A wound causes a loss of substance or of biological fluid (blood or exudate). When applied to a wound, the prior art dressings that are made of calcium alginate fibres begin by absorbing the biological fluid which oozes, or exudes, the water molecules of the fluid collecting between the molecules of the alginate.

Once swollen by absorption, the dressing undergoes gel formation through ion exchange. In the case of calcium alginate fibres, these yield $Ca^{2+}$ ions to the biological fluid, and the latter yields $Na^+$ ions in return. This ion exchange, the principal mechanism of action, constitutes the factor triggering the activation of platelets, macrophages and fibroblasts, as manifested by activation of the physiological processes of haemostasis and tissue repair.

The haemostatic action is due to the mechanical pressure action created by the swelling during hydration and to the biological action resulting from this rapid and intense release of calcium ions, thus inducing platelet aggregation and stimulation of clotting factors. Moreover, the fibres constitute a matrix making it possible to structure and strengthen the network of the blood clot.

As the equilibrium between calcium and sodium establishes itself, the alginate fibres lose some of their crystalline structure, leading to gel formation of the fibres. The gel formation of the dressing ensures that it does not adhere to the underlying tissues. However, it damages and more generally affects the integrity of the mechanical structure of the dressing, e.g., a wick, so that the dressing cannot be removed from the wound in one piece and without pain.

The aforementioned undesirable features of the prior art dressings are directly related to the underlying production material and method. The prior art dressings are obtained from a continuous card ribbon which is cut to the desired length. The card ribbon is obtained from a card web which is passed through a static cone (the funnel of a whistle) whose function is to gather the fibres and to give the web a cylindrical shape. Two motorized press rollers or calenders allow the material to be pulled and its shape to be fixed, before the wicks or tampons are formed, placed in bags or containers and then in boxes.

In this prior art production method, the fibres constituting the ribbon do not present cohesion in the direction of width, which causes them to slide in the direction of length. The dressing therefore cannot be removed from wounds in its entirety and without causing pain.

BRIEF SUMMARY OF THE INVENTION

An object of the present invention is to provide a dressing product which has the same desirable properties as that of the prior art dressing products but without their undesirable features. That is, the dressing product should be more easily removed from a wound in its entirety and without causing pain.

This object is achieved in a dressing product comprising fibres of a spinnable polymer forming a twisted ribbon. By virtue of this twisting, the fibres, in particular at the periphery of the ribbon, are connected to one another so as to afford better mechanical cohesion and a smoother outer appearance, without affecting the action of absorption, dilation and gel formation for extracting the biological fluid, nor the action of retention of proteins and other cellular and bacterial waste matter which would impede the phenomenon of cicatrization.

The twisted ribbon advantageously comprises a traceability filament, which is made possible by virtue of the cohesion of the fibres. The benefit of such a filament is that this avoids leaving the dressing in a body cavity. In some embodiments, it is a radiopaque filament, since radiological detection is the customary procedure when there is any doubt as to whether all the products have been removed after a surgical intervention.

In some embodiments, the spinnable polymer is a spinnable alginate of a metal chosen from the family of polyvalent metals, except for magnesium. In some embodiments, the spinnable alginate is calcium alginate.

The present invention is directed to the means of improving the cohesion of the fibres within the dressing product. The technique for obtaining a card ribbon or web of polymer fibres emerging from the card, in particular of metal alginate, and more particularly of calcium alginate, is well established and thus will not be discussed herein.

The present invention also concerns a method for producing a dressing product useful for covering/protecting a wound with biological fluid. The dressing product producing method comprises the steps of forming a substantially cylindrical ribbon from fibres of a spinnable polymer by driving the fibres in rotation downstream of a card, and by passing the fibres through a twisting die to obtain a twisted ribbon. Preferably, the method further comprises the step of passing the twisted ribbon through a pressure calender for fixing the shape of the fibres.

In the case where a ribbon of fibres is driven in rotation, before and after it is driven in rotation and twisted, it is passed through an upstream roller and downstream roller in order to limit the zone of twisting. Thus, the downstream calender for limiting twisting can serve as a pressure calender.

In some embodiments, the fibres of a web emerging from the card are also driven in rotation. The web is advantageously guided before being driven in rotation.

Finally, the present invention concerns a system for twisting the fibres of a spinnable polymer to form a dressing product useful for covering/protecting a wound with biological fluid. The system or equipment comprises a conical bowl for driving the fibres in rotation with a twisting die in its narrowed downstream part. The system further comprises a means for driving the bowl in rotation, for example, a wheel gear or a drive belt. The system further advantageously comprises a calender for pressing and fixing the shape of the fibres of the dressing product.

Other characteristics and advantages will become apparent to one of ordinary skill in the art upon reading and understanding the preferred embodiments described below with reference to the following drawings.

DETAILED DESCRIPTION OF THE INVENTION

Figure 1:
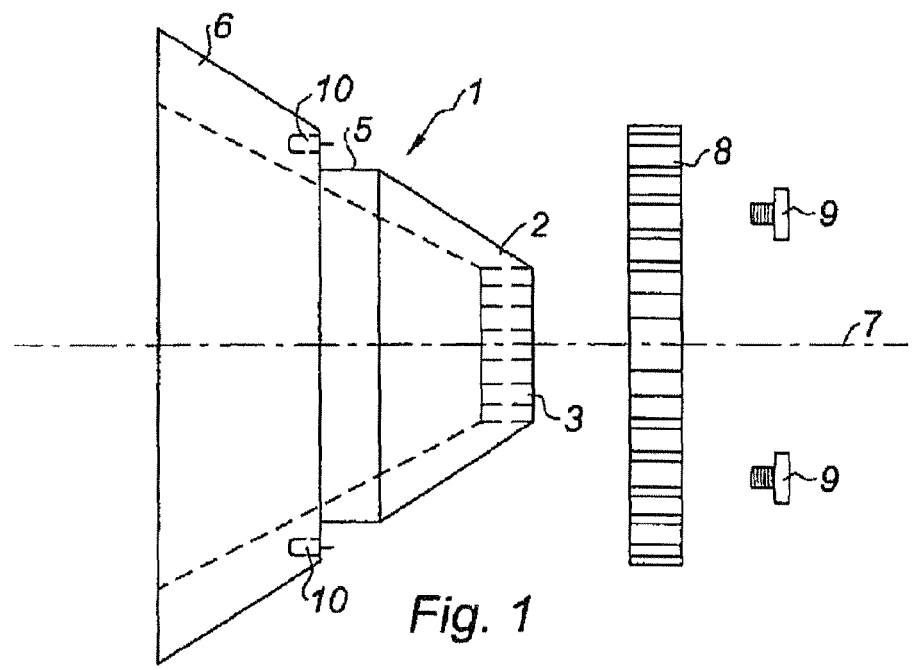
FIG. 1 is a side view of the bowl for driving the equipment in rotation.
Figure 2:
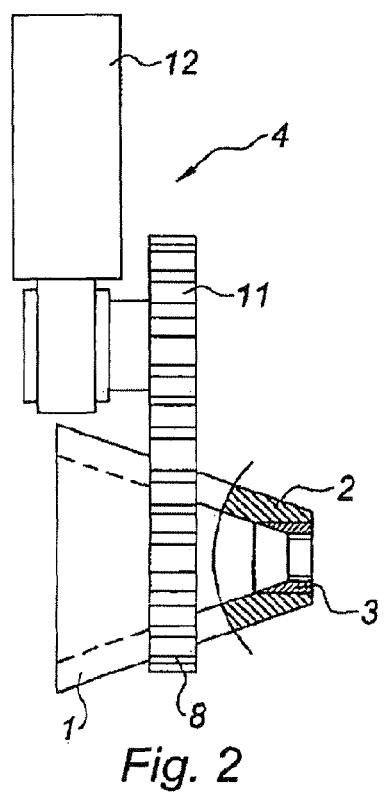
FIG. 2 is a side view of the equipment with a wheel gear.

The equipment for twisting the fibres will now be described with reference to FIGS. 1-5. As illustrated in FIG. 1, the equipment comprises a bowl 1, which drives the fibres in rotation, and which can also be referred to as a funnel, of conical shape, made of plastic or of metal, having a twisting die 3 in its narrowed downstream part 2. The whole arrangement can be referred to as a whistle. The bowl 1 can be driven in rotation by a gear mechanism 4, as shown in FIG. 2.

An annular shoulder 5 is formed in the wall 6 of the bowl 1, overall in a transverse plane perpendicular to the axis 7 of the bowl 1, in order to receive the driven pinion 8 of the gear mechanism 4. The driven pinion 8 is fixed by screws 9 which are screwed into orifices 10 in the wall 6 of the bowl 1. The driven pinion 8 meshes with a driving pinion 11, itself driven by a motor 12, so as to form a wheel gear 8, 11.

In some embodiments, in place of the wheel gear 8, 11, a drive belt is mounted around a driving pulley, integral with the shaft of the motor 12. Further, in some embodiments, a driven pulley is mounted on the bowl 1 in place of the pinion 8.

Figure 3:
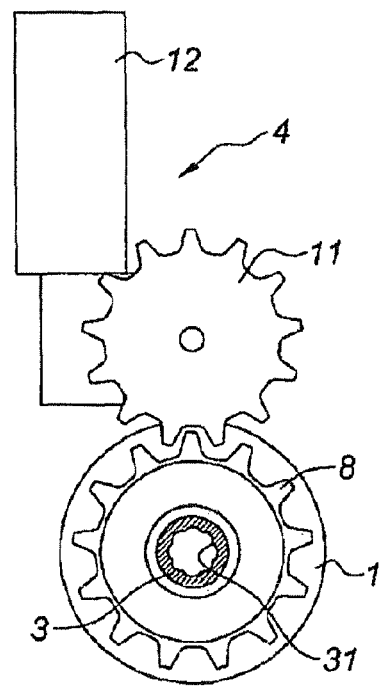
FIG. 3 is a front view of the equipment in FIG. 2, from the downstream end.

The die 3 is a cylindrical die with grooves 31, as shown in FIG. 3. Alternatively, it could have an entirely different design making it possible to secure the fibres and to drive them in a twisting movement, or, to comb them at the periphery to improve the appearance of the final dressing ribbon. It could also be frustoconical. The die is made of stainless steel, for example.

Figure 4:
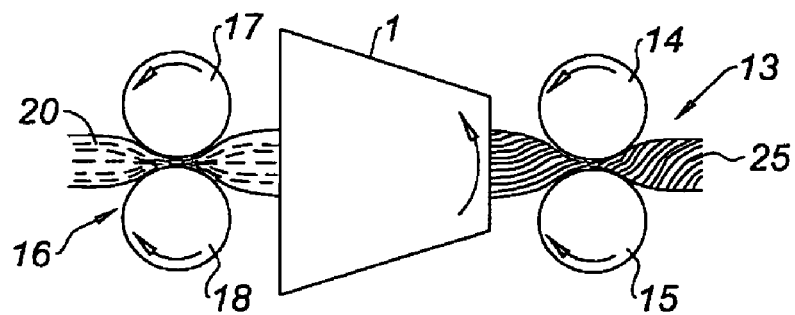
FIG. 4 is a partial view of the equipment according to the invention for a ribbon of fibres to be twisted.
Figure 5:
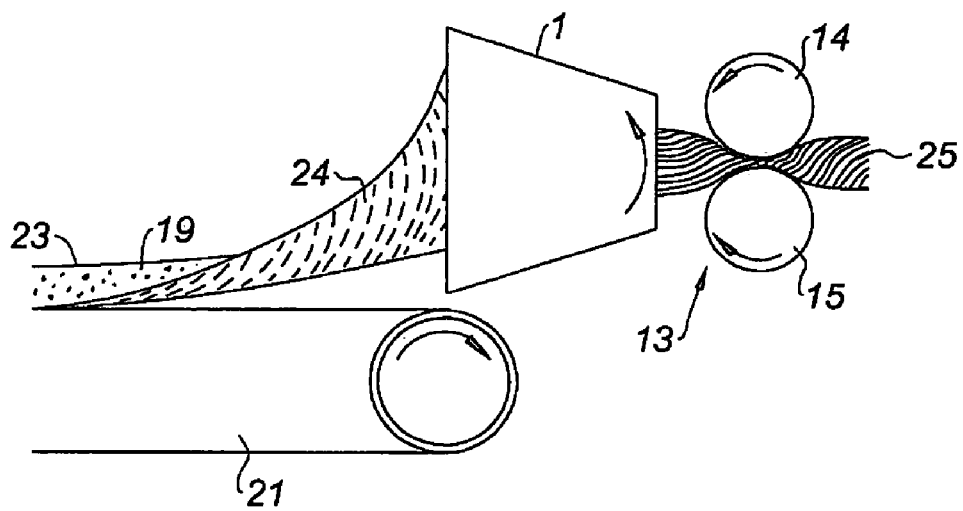
FIG. 5 is a partial side view of the equipment according to the invention for a web emerging from a card.

As shown in FIG. 4, the equipment further comprises a downstream calender 13 and an upstream calender 16. The downstream calender 13 comprises two motorized press rollers 14, for pressing the ribbon emerging from the die 3 and for fixing the shape of the fibres. The downstream roller 13 is used alone when a web 19 emerging from the card is driven in rotation, as illustrated in FIG. 5. When a ribbon of fibres 20 is driven in rotation, the upstream calender 16 thus formed by two motorized press rollers 17, 18 is also used. As such, by passing the ribbon through the two calenders 13, 16 arranged on either side of the bowl 1 and by blocking the ribbon of fibres there, it is possible to limit the zone of twisting.

Note that the rollers 14, 15, 17, 18 also serve to pull the fibres. With regard to the pressing and fixing in shape of the ribbon emerging from the die, and to provide precise figures, the pressure can vary from 0.5 to 4 bar for densities ranging from 4 to 9 grams per meter and for ribbon diameters ranging from 0.5 to 2 centimetres.

Figure 6:
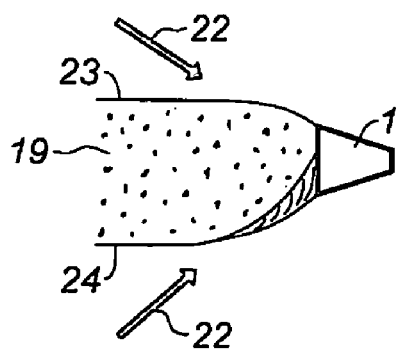
FIG. 6 is a top view, on a smaller scale, of the equipment from FIG. 5.
Figure 7:
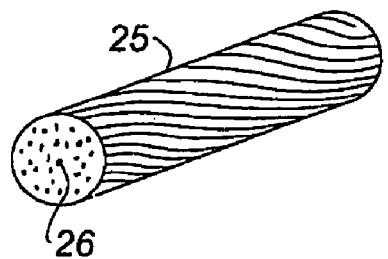
FIG. 7 is a perspective view of an embodiment of the dressing product produced according to the method and equipment of the present invention.

In the case where the dressing product is obtained directly from a web of fibres 19 emerging from the card, the equipment comprises members for guiding the web. These members include a conveyor belt 21 and nozzles, indicated by arrows 22 in FIG. 6, emitting jets of air at the borders 23, 24 of the web 19, in the direction of its centre. The width of the web influences the appearance of the dressing ribbon; the greater the width, the greater the twisting and the greater the strength of the ribbon.

Preferably, the die 3 has a diameter slightly smaller than that of the dressing ribbon which one wishes to produce. For example, a dressing ribbon measuring 1 cm in diameter can be obtained using a die whose cross section of passage has a diameter of 0.5 to 1.5 cm. A cross section of 0.6 to 0.8 cm is preferable.

To obtain the dressing ribbon, downstream of a card from which a web emerges, the fibres, i.e., directly those of the web 19 or those of a ribbon 20 which has been formed beforehand after folding of the web (see, FIG. 4), are introduced into and driven in rotation in the bowl 1. The fibres then pass through the die 3 where they are twisted to form a twisted fibrous ribbon 25, are pressed, and their shape is fixed in the calender 13.

By virtue of the twisting and peripheral combing, the dressing ribbon will retain better cohesion, particularly in the direction of width, thus avoiding sliding in the lengthwise direction, this making it easier to remove it from the wound completely and without causing pain. The ribbon 25 advantageously comprises a traceable filament 26 placed at the centre and entirely surrounded by fibres, hence invisible from the outside. Although traceable, escape is impossible.

In each case of producing the dressing ribbon 25, either from the web 19 or ribbon 20, the material moves at constant speed through the equipment and must not experience acceleration, so as not to cause stretching, or even tearing.

The speed of rotation of the assembly made up of the bowl and the die must be sufficiently fast. Depending on the speed of advance of the material, it is between 50 and 700 revolutions per minute. For example, a speed of the order of 300 revolutions per minute is suitable for an advance of 12 to 36 meters per minute, and preferably of 30 meters per minute.

The humidity of the material during its shaping also plays an important role in the appearance of the final product. It must be between 28 and 40%, preferably between 30 and 35%. Below these values, the fibres are too dry and do not allow the desired shape to be maintained and, above these values, the fibres are too heavy and too sticky, the ribbon losing its cylindrical shape and remaining flat.

Tables 1 and 2 below, which summarize the results of tests of tensile strength in the direction of width, reveal the increase in the mechanical strength of the dressing product due to the inventive shaping procedure which has just been described.

These tests were conducted using a card web with a width of 1 meter, a density of 20 g per m$^3$ and a humidity of 30%. As regards the card web treated according to the invention, the speed of advance was 24 meters per minute, the inlet diameter of the bowl was 11 centimetres, its length 5 centimetres, its outlet diameter (die diameter) 0.7 centimetre. The speed of rotation of the assembly was 300 revolutions per minute and the pressure between the rollers was 1 bar.

In both cases, i.e. the conventional ribbon and the ribbon of the prior art, a ribbon was formed which was cut into eight sections of 4 cm in length and whose tensile strength was measured, in the direction of width of the ribbon, between the two jaws of a dynamometer.

TABLE 1

Conventional Ribbon

| | Tensile strength in width direction in m.kg.s$^{-2}$ (Newton) |
|---|---|
| Section 1 | 0.44 |
| Section 2 | 0.56 |
| Section 3 | 0.52 |
| Section 4 | 0.38 |
| Section 5 | 0.39 |
| Section 6 | 0.49 |
| Section 7 | 0.31 |
| Section 8 | 0.48 |
| Average | 0.45 |

TABLE 2

Twisted Ribbon

| | Tensile strength in width direction in m.kg.s$^{-2}$ (Newton) |
|---|---|
| Section 1 | 0.61 |
| Section 2 | 0.74 |
| Section 3 | 0.89 |
| Section 4 | 0.58 |
| Section 5 | 0.70 |
| Section 6 | 1.12 |
| Section 7 | 0.92 |
| Section 8 | 0.96 |
| Average | 0.82 |

On average, the tensile strength of the dressing product according to the invention is almost twice stronger than that of the conventional ribbon.

Although the present invention and its advantages have been described in detail, it should be understood that the present invention is not limited to or defined by what is shown or described herein. As one of ordinary skill in the art will appreciate, various changes, substitutions, and alterations could be made or otherwise implemented without departing from the principles of the present invention. Accordingly, the scope of the present invention should be determined by the following claims and their legal equivalents.

The invention claimed is:

1. A method for producing a dressing product useful for covering a moist wound, comprising the steps of:
    forming a substantially cylindrical ribbon from fibres of a spinnable polymer by driving the fibres in rotation downstream of a card, and by passing the fibres through a twisting die to obtain a twisted ribbon, in which, when a ribbon of fibres is driven in rotation, before and after it is driven in rotation and twisted, it is passed through an upstream calender and downstream calender, thereby limiting the zone of twisting.

2. The method according to claim 1, further comprising the step of:
    passing the twisted ribbon through a pressure calender for fixing the shape of the fibres.

3. The method according to claim 1, in which the downstream calender serves as a pressure calender.

4. A method for producing a dressing product useful for covering a moist wound, comprising the steps of:
    forming a substantially cylindrical ribbon from fibres of a spinnable polymer by driving the fibres in rotation downstream of a card, and by passing the fibres through a twisting die to obtain a twisted ribbon; and
    driving the fibres of a web emerging from the card in rotation.

5. The method according to claim 4, further comprising the step of:
    guiding the web before the driving step.

6. The method according to claim 5, in which the web is guided by the action of jets of air on the borders of the web.

* * * * *